United States Patent
Bagger-Sjöbäck et al.

(10) Patent No.: US 11,801,173 B2
(45) Date of Patent: Oct. 31, 2023

(54) ABSORBENT HYGIENIC ARTICLE FOR ABSORBING BODY FLUIDS

(71) Applicant: Essity Hygiene and Health Aktiebolag, Gothenburg (SE)

(72) Inventors: Anna Bagger-Sjöbäck, Gothenburg (SE); Magdalena Hörle, Gothenburg (SE); Philip Blomström, Gothenburg (SE); Lars Fingal, Gothenburg (SE); Anna Nihlstrand, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 17/783,332

(22) PCT Filed: Dec. 20, 2019

(86) PCT No.: PCT/SE2019/051330
§ 371 (c)(1),
(2) Date: Jun. 8, 2022

(87) PCT Pub. No.: WO2021/126034
PCT Pub. Date: Jun. 24, 2021

(65) Prior Publication Data
US 2023/0136549 A1    May 4, 2023

(51) Int. Cl.
*A61F 13/15* (2006.01)
*A61F 13/511* (2006.01)
(Continued)

(52) U.S. Cl.
CPC ......... *A61F 13/51121* (2013.01); *A61L 15/28* (2013.01); *D04H 1/26* (2013.01);
(Continued)

(58) Field of Classification Search
CPC ...... A61F 13/51121; A61F 2013/15406; A61F 2013/15463; A61F 2013/15983;
(Continued)

(56) References Cited

U.S. PATENT DOCUMENTS

| 5,486,167 A | 1/1996 | Dragoo et al. |
| 6,017,833 A | 1/2000 | Reiner et al. |

(Continued)

FOREIGN PATENT DOCUMENTS

| CN | 1126067 A | 7/1996 |
| CN | 1137585 A | 12/1996 |

(Continued)

OTHER PUBLICATIONS

International Preliminary Report on Patentability (PCT/IPEA/409) dated Mar. 2, 2022 for International Application No. PCT/SE2019/051330. (7 pages).

(Continued)

*Primary Examiner* — Jacqueline F Stephens
(74) *Attorney, Agent, or Firm* — BUCHANAN INGERSOLL & ROONEY PC

(57) ABSTRACT

An absorbent hygienic article for absorbing body fluids, the article including a liquid absorbent top layer and a backing layer, the top layer and the backing layer being made from roll materials and being joined together. The top layer is constituted by a cellulosic fibrous web, the fibres in the cellulosic fibrous web being constituted by a mixture of cellulose fibres, the mixture including regenerated cellulose fibres or natural cellulose staple fibres and cellulose pulp fibres, the cellulosic fibrous web being a foam-formed, hydroentangled cellulosic fibrous web.

16 Claims, 1 Drawing Sheet

(51) Int. Cl.
*D04H 1/4382* (2012.01)
*A61L 15/28* (2006.01)
*D04H 1/26* (2012.01)
*D04H 1/425* (2012.01)
*D04H 1/4258* (2012.01)
*D04H 1/492* (2012.01)
*A61F 13/47* (2006.01)
*A61F 13/51* (2006.01)

(52) U.S. Cl.
CPC .......... *D04H 1/425* (2013.01); *D04H 1/4258* (2013.01); *D04H 1/43835* (2020.05); *D04H 1/492* (2013.01); *A61F 2013/15406* (2013.01); *A61F 2013/15463* (2013.01); *A61F 2013/15983* (2013.01); *A61F 2013/4708* (2013.01); *A61F 2013/51021* (2013.01); *A61F 2013/51038* (2013.01); *A61F 2013/51134* (2013.01); *D10B 2509/02* (2013.01); *D10B 2509/026* (2013.01)

(58) Field of Classification Search
CPC .... A61F 2013/4708; A61F 2013/51021; A61F 2013/51038; A61F 2013/51134; D04H 1/26; D04H 1/425; D04H 1/4258; D04H 1/492; D10B 2509/02; D10B 2509/026
See application file for complete search history.

(56) References Cited

U.S. PATENT DOCUMENTS

| | | | |
|---|---|---|---|
| 9,161,865 | B2 | 10/2015 | Paveletzke et al. |
| 2003/0213108 | A1 | 11/2003 | Strandqvist |
| 2005/0155199 | A1 | 7/2005 | Stralin et al. |
| 2010/0274208 | A1* | 10/2010 | Gabrielii .......... A61F 13/51108 604/378 |
| 2013/0313149 | A1* | 11/2013 | Hird .................. A61L 15/24 206/459.5 |
| 2014/0170402 | A1 | 6/2014 | Knowlson et al. |
| 2015/0083354 | A1 | 3/2015 | Strandqvist |
| 2017/0203542 | A1 | 7/2017 | Ramaratnam et al. |
| 2018/0355527 | A1 | 12/2018 | Strandqvist et al. |
| 2018/0363177 | A1 | 12/2018 | Strandqvist |
| 2019/0276958 | A1 | 9/2019 | Konishi |
| 2023/0028309 | A1 | 1/2023 | Rössler et al. |
| 2023/0042528 | A1 | 2/2023 | Bagger-Sjöbäck et al. |

FOREIGN PATENT DOCUMENTS

| | | | |
|---|---|---|---|
| CN | 1948613 | A | 4/2007 |
| CN | 100558980 | C | 11/2009 |
| CN | 103118646 | A | 5/2013 |
| CN | 11191692 | A | 8/2019 |
| EP | 3382078 | A1 | 10/2018 |
| JP | H1193055 | A | 4/1999 |
| WO | 9602701 | A1 | 2/1996 |
| WO | 03069038 | A1 | 8/2003 |
| WO | 03083197 | A1 | 10/2003 |
| WO | 2005002842 | A1 | 1/2005 |
| WO | WO 2005007962 | * | 1/2005 ......... A61F 13/5323 |
| WO | 2005042819 | A2 | 5/2005 |
| WO | 2006001739 | A1 | 1/2006 |
| WO | 2010021572 | A1 | 2/2010 |
| WO | 2012090130 | A2 | 7/2012 |
| WO | 2012150902 | A1 | 11/2012 |
| WO | 2017079169 | A1 | 5/2017 |
| WO | 2018065668 | A1 | 4/2018 |

OTHER PUBLICATIONS

International Preliminary Report on Patentability (PCT/IPEA/409) dated Mar. 2, 2022 for International Application No. PCT/SE2019/051331. (8 pages).
International Search Report (PCT/ISA/210) and Written Opinion (PCT/ISA/237) dated Sep. 2, 2020, by the Swedish Patent Office as the International Searching Authority for International Application No. PCT/SE2019/051330. (16 pages).
International Search Report (PCT/ISA/210) and Written Opinion (PCT/ISA/237) dated Sep. 2, 2020, by the Swedish Patent Office as the International Searching Authority for International Application No. PCT/SE2019/051331. (15 pages).
Written Opinion of the International Preliminary Examining Authority (PCT/IPEA/408) dated Dec. 1, 2021 by the European Patent Office as the International Searching Authority for International Application No. PCT/SE2019/051330. (5 pages).
Written Opinion of the International Preliminary Examining Authority (PCT/IPEA/408) dated Dec. 1, 2021 by the Swedish Patent Office as the International Searching Authority for International Application No. PCT/SE2019/051331. (7 pages).
Corrected International Search Report (PCT/ISA/210), Corrected Written Opinion (PCT/ISA/237), Communication in Cases for Which No Other Form is Applicable (PCT/ISA/224) dated Feb. 1, 2021 by the Swedish Patent Office as the International Searching Authority for International Application No. PCT/SE2020/051158. (12 pages).
Office Action issued in Chinese Patent Application No. 201980102567.0, dated Nov. 4, 2022, with English Translation (24 pages).
Notice of Allowance issued in U.S. Appl. No. 17/783,335, dated Jan. 26, 2023 (17 pages).
Notification of the First Office Action dated Jan. 20, 2023, by the Chinese Patent Office in corresponding Chinese Patent Application No. 202080083295.7, and an English Translation of the Office Action. (15 pages).
Decision of Rejection issued in Chinese Patent Application No. 2019801025543 dated Mar. 2, 2023, with English Translation (12 pages).
Office Action dated Jun. 8, 2023, in Chinese Patent Application No. 202080083295.7 and English translation of the Office Action. (15 pages).

* cited by examiner

ABSORBENT HYGIENIC ARTICLE FOR ABSORBING BODY FLUIDS

TECHNICAL FIELD

The invention pertains to an absorbent hygienic article for absorbing body fluids, the article comprising a liquid absorbent top layer and a backing layer, the top layer and the backing layer being made from roll materials and being joined together.

BACKGROUND

In the field of disposable absorbent hygienic articles such as disposable panty liners, bibs, a seat covers, place mats, underpanties, bed protectors, and the like which are thrown away after a single use, it is a rising concern to minimize the environmental impact of such articles. Hence, it is a desire that disposable hygienic articles may be made using a minimum of oil based polymeric materials.

However, conventionally used plastic materials have functional advantages, e.g. as they are non-absorbent and provide dry surface materials desirable for articles which are placed in close contact with the skin of a wearer.

An object of the present disclosure may therefore be to offer an absorbent hygienic article having a non-oil based body-contacting material without losing functionality.

A further object may be to provide an absorbent hygienic article which is dry against skin and which efficiently utilizes the available absorption capacity of the absorbent hygienic article.

SUMMARY

One or more of the above objects may be achieved with an absorbent hygienic article in accordance with claim 1. Further embodiments are set out in the dependent claims, in the following description and in the drawings.

An absorbent hygienic article for absorbing body fluids as disclosed herein comprises a liquid absorbent top layer and a backing layer, the top layer and the backing layer being made from roll materials and being joined together. The top layer is constituted by a cellulosic fibrous web, the fibres in the cellulosic fibrous web being constituted by a mixture of cellulose fibres, the mixture comprising regenerated cellulose fibres and/or natural cellulose staple fibres and cellulose pulp fibres, the cellulosic fibrous web being a foam-formed, hydroentangled cellulosic fibrous web.

The absorbent fibrous webs which are suitable for use in the absorbent hygienic articles as disclosed herein have a large proportion of the fibres oriented at an angle to the plane of the web such that the fibres extend at least partly in the Z-direction of the web. As used herein the Z-direction of the web is perpendicular to the X-direction and the Y-direction which define the planar extension of the web. The Z-direction is also referred to herein as the thickness direction of the web. The Z-directionality of the fibres in the web may be influenced by the web being a hydroentangled web. Hydroentangling involves exposing the formed web to high-pressure water jets which move fibres out of the plane of the web. Hydroentangling may be performed on one side of the foam-formed web or on both sides. The Z-directionality of the fibres in the web may also be enhanced during wetforming of the web by dewatering the web from both sides, e.g. as disclosed in WO 2018/065668 A1. Depending on the forming wires used and the dewatering speed, the webs formed according to the method in WO 2018/065668 A1 may be provided with a high degree of like sidedness, which may be advantageous in some applications.

The absorbent fibrous webs as used herein are foam-formed webs. Foam-forming is a type of wetforming which involves dispersing the fibres in a foamed liquid containing water and a surfactant. Foam-forming creates bulky high porosity webs.

The cellulosic fibrous web may have been foam-formed as a single unitary web which has subsequently been hydroentangled. However, the cellulosic fibrous webs may comprise two or more layers of foam-formed webs which have been hydroentangled together to form a coherent cellulosic fibrous web. In the case where two or more layers of foam-formed webs make up the final hydroentangled web, the layers may have the same or different fibre compositions. Furthermore, the layers may have the same or different basis weights and may have the same or different bulk.

The cellulose pulp fibres in the absorbent fibrous webs used in the absorbent hygienic articles as disclosed herein are preferably wood pulp fibres as wood pulp fibres can be economically manufactured from readily available raw material, are well known in the art and have good absorption and liquid distribution properties. The cellulose pulp fibres are considerably shorter than the regenerated cellulose fibres and/or natural cellulose staple fibres which form a fibrous network for capturing and containing the cellulose pulp fibres.

Wood pulp fibres as referred to herein comprise pulp fibres from chemical pulp, e.g. kraft, sulphate or sulphite, mechanical pulp, thermo-mechanical pulp, chemo-mechanical pulp and/or chemo-thermo-mechanical pulp, abbreviated as CTMP. Pulps derived from both deciduous (hardwood) and coniferous (softwood) can be used. Cellulose pulp fibres may also be derived from non-wood plants, e.g. cereal straws, bamboo, jute or sisal. The fibres or a portion of the fibres may be recycled fibres, which may belong to any or all of the above categories.

Additives such as softeners, e.g. quaternary ammonium compounds, dry-strength agents or wet-strength agents may be added in order to facilitate manufacturing of the cellulosic fibrous web or to adjust the properties thereof. However, for some embodiments of the cellulosic fibrous web, the absorbent fibrous web may be so strong in itself, that there is no need for a dry strength agent or and/or a wet strength agent to improve strength.

As all the fibres used in the absorbent fibrous webs as disclosed herein are of cellulosic origin, the absorbent fibrous webs as disclosed herein are made from renewable raw materials.

Further, the absorbent fibrous webs as disclosed herein have a textile-like character, which is appreciated in many user situations, e.g. for hygiene articles which are intended to be placed in close contact with the skin of a user. Products, such as panty liners, made of the cellulosic absorbent fibrous webs as disclosed herein may possess the requisite strength properties while at the same time being soft and comfortable against the skin of a user. The textile-like character of the cellulosic fibrous webs may be felt both in a dry and in a wet state.

The backing layer is preferably a liquid impermeable backing layer or a backing layer having high resistance to liquid penetration. It may be desirable that the backing layer is a breathable backing layer, as known in the art. It may also be preferred that the backing layer is derived from renewable raw materials.

The term "cellulosic staple fibres" as used herein includes man-made and/or natural cellulosic fibres. Examples of man-made cellulosic fibres, also called regenerated cellulosic fibres, are viscose fibres and lyocell. Examples of natural cellulosic fibres are seed hair fibres, e.g. cotton, kapok, and milkweed; leaf fibres e.g. sisal, abaca, pineapple, and New Zealand hemp; or bast fibres e.g. flax, hemp, jute and kenaf. The natural cellulosic staple fibres may be cut to staple length or may have a natural staple length, such as cotton.

If the cellulosic staple fibres are man-made fibres, they can be treated with spin finish and crimped, but this is not necessary for the type of foam-forming processes used to produce the absorbent fibrous webs described in the present disclosure.

Cutting of a fibre bundle to staple fibres is normally made to produce in a single cut length for the fibres. The fibre length can be altered by varying the distances between the knives of the cutting wheel. Thereby the fibre length can be set depending on the planned use of the staple fibres.

The regenerated cellulose fibres and/or the natural cellulose staple fibres in the webs used in the absorbent hygienic articles as disclosed herein may be staple fibres having a length within the range of from 2 to 20 millimeter, such as in the range of from 5 to 15 millimeter, such as in the range of from 5 to 12 millimeter, such as in the range of from 6 to 10 millimeter. The linear density of the regenerated cellulose fibres and/or the natural cellulose staple fibres used in the webs as disclosed herein may be in the range of from 0.3 to 3 dtex, such as in the range of from 0.5 to 2.4 dtex, such as in the range of from 0.8 to 2.0 dtex.

The regenerated cellulose fibres may be viscose fibres or lyocell fibres.

The mixture of cellulose fibres may be constituted by 2 to 50% by weight of regenerated cellulose fibres and/or natural cellulose staple fibres based on a total weight of the mixture of cellulose fibres, such as 2 to 40% by weight of a total weight of the mixture of cellulose fibres, or such as 5 to 25% by weight of a total weight of the mixture of cellulose fibres, or such as 10 to 20% by weight of the mixture of cellulose fibres.

The top layer of the absorbent hygienic article as disclosed herein may have a basis weight of from 30 gsm to 100 gsm.

The absorbent fibrous web may have a bulk in the range of 7.5 to 11 cm$^3$/g, such as from 7 to 10 cm$^3$/g or from 8 to 9 cm$^3$/g. A bulk within these ranges indicates that the absorbent fibrous web is lofty and porous. A high bulk value is an indication that a foam-forming process has been used when producing the absorbent fibrous web.

The absorbent hygienic articles as disclosed herein have excellent properties with regard to surface dryness. The absorbent hygienic articles preferably have a rewet of less than 1 gram, such as a rewet of less than 0.8 gram or a rewet of less than 0.7 gram as measured according to the method disclosed herein. It has surprisingly been found that the absorbent hygienic articles as disclosed herein, although having an all-cellulosic top layer, has excellent rewet properties.

The cellulosic fibrous web in the absorbent hygienic articles as disclosed herein may have a liquid spreading capacity in a machine direction of the cellulosic fibrous web of 75 millimeters or more as measured after three insults of test liquid in accordance with the test method disclosed herein.

The cellulosic fibrous web in the absorbent hygienic articles as disclosed herein may have a liquid spreading capacity in a cross machine direction of the cellulosic fibrous web of 30 millimeters or more as measured after a first insult of test liquid and of 45 millimeters or more as measured after two insults of test liquid, the measurements being made in accordance with the test method disclosed herein.

The machine direction of the sample used in the method corresponds to the length direction of the absorbent hygienic article and the cross machine direction of the sample corresponds to the cross direction or width direction of the absorbent hygienic article.

A user-facing surface of the absorbent hygienic article may be provided with a pattern, the pattern being an embossed pattern, a dimpling pattern, a printed pattern or a combination of one or more of an embossed pattern, a dimpling pattern, and a printed pattern.

The absorbent hygienic article as disclosed herein may have embossings arranged in a user-facing surface of the top layer. The embossings serve to locally compress the cellulosic fibrous web to create a compacted structure with smaller pores within the areas of the embossings. Such embossings may be used to further control liquid distribution in the absorbent hygienic article. In addition to or instead of functional embossings, the absorbent hygienic article may be provided with decorative embossings, functional and/or decorative print, etc., as known in the art.

The cellulosic fibrous web which is used in the absorbent hygienic articles as disclosed herein have high liquid spreading capability both in the machine direction of the web and in the cross machine direction of the web. A sample of the cellulosic fibrous web having a length in the machine direction of 100 millimeters and a width in the cross machine direction of 50 millimeters and a basis weight of 50 gsm to 70 gsm may have a wet area of 3500 mm$^3$ or more, such as a wet area of 4000 mm$^3$ as measured according to the test method as disclosed herein.

As the sample is cut to a width of 50 millimeters in the cross machine direction, when tested according to the method as disclosed herein which involves three depositions of 0.5 ml test liquid, the test liquid will have spread all the way to the longitudinal edges in all samples made from the cellulosic fibrous web material as disclosed herein after the third deposition of test liquid has been made.

The absorbent hygienic article as disclosed herein may be a simple two-layer article, the top layer and the backing layer are the only constituent layers of the absorbent hygienic article.

The absorbent hygienic article may be a panty liner, such as an ultra-thin panty liner. Ultra-thin panty liners are panty liners having a thickness below 1.0 millimetres such as from 0.3 millimetres to 0.8 millimetres or from 0.5 millimetres to 0.7 millimetres.

The absorbent hygienic article may be any kind of absorbent hygienic article where a limited absorption capacity is required such an underwear protector for male or female users, an underarm protector (sweat protector), a bib, a seat cover, a place mat, under pants, or a bed protector.

A user-facing surface of the absorbent hygienic article may be provided with a pattern, the pattern being an embossed pattern, a dimpling pattern, a printed pattern or a combination of one or more of an embossed pattern, a dimpling pattern, and a printed pattern.

BRIEF DESCRIPTION OF THE DRAWINGS

The absorbent hygienic articles as disclosed herein will be further explained hereinafter by means of non-limiting examples and with reference to the appended drawings wherein.

DETAILED DESCRIPTION

It is to be understood that the drawings are schematic and that individual components or features, such as layers of material are not necessarily drawn to scale. The panty liner shown in the figures is provided as an example only and should not be considered limiting to the invention as disclosed herein. In particular, it is to be understood that shape and dimensions are non-essential features of the invention and may be varied within the scope of the claims. Furthermore, the absorbent hygienic article as disclosed herein may be any type of absorbent hygienic article where only a limited amount of absorbency is required such as a panty liner for male or female users, an under-arm protector, a bib, a seat cover, a place mat, under panties, or a bed protector.

Figure 1:
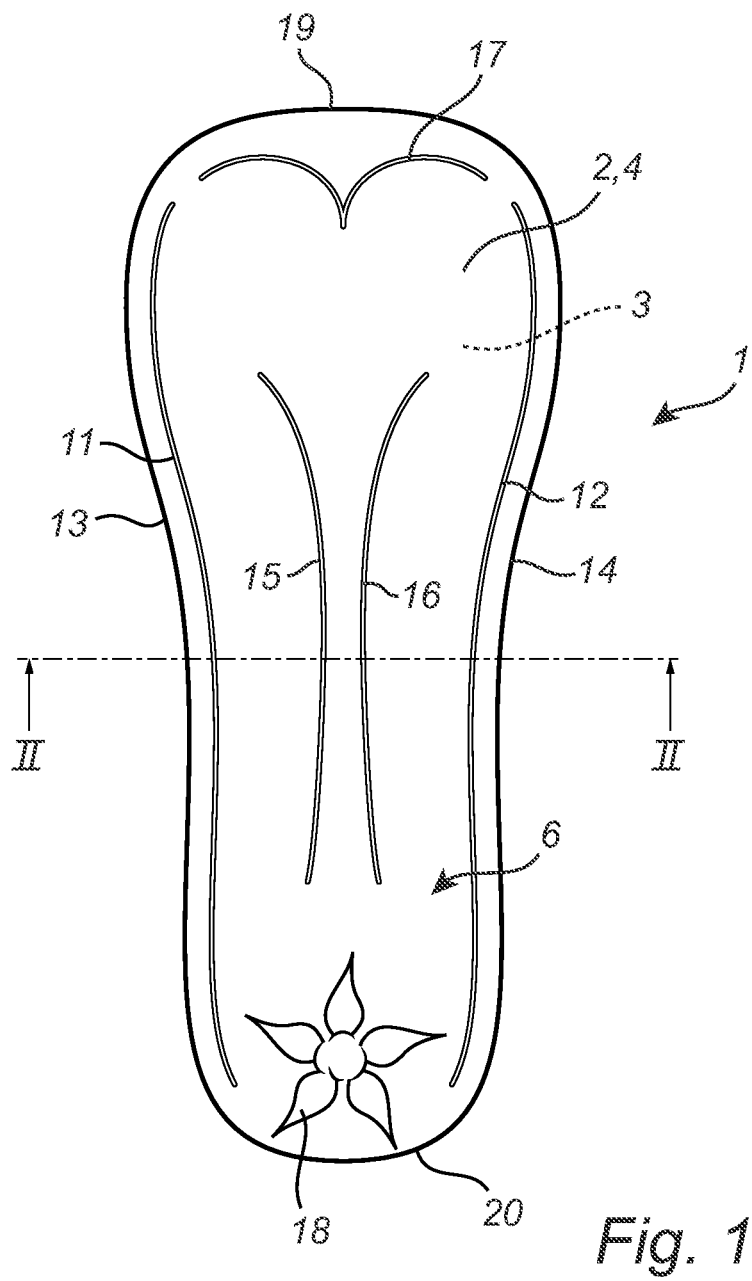
FIG. 1 shows a panty liner.

The absorbent hygienic article 1 for absorbing body fluids which is shown in FIG. 1 is a panty liner comprising a liquid absorbent top layer and backing layer 3. The top layer 2 and the backing layer 3 are made from roll materials and are joined together, such as by adhesive, ultrasonic welding or mechanical welding using embossing and pressure.

The top layer 2 is constituted by a cellulosic fibrous web 4, as disclosed herein. Accordingly, the fibres in the cellulosic fibrous web 4 are constituted by a mixture of cellulose fibres. The fibre mix comprises regenerated cellulose fibres, such as viscose fibres and cellulose pulp fibres such as wood pulp fibres. The cellulosic fibrous web is a foam-formed, hydroentangled cellulosic fibrous web. The regenerated cellulose fibres may be staple fibres, as disclosed herein.

The backing layer 3 is a liquid barrier layer which is arranged on the surface of the panty liner 1, which is intended to face away from the wearer of the panty liner 1 during use of the panty liner 1, also referred to herein as the garment-facing surface 5 of the panty liner 1. The garment-facing surface 5 is opposite a wearer-facing surface 6. The backing layer 3 is preferably fluid impermeable. However, liquid barrier materials which are only resistant to fluid penetration may be used for the backing layer 3, particularly as only small amounts of body fluid are expected to be taken up by the absorbent hygienic articles as disclosed herein. The backing layer 3 may be a thin, flexible, liquid impermeable plastic film, but liquid impermeable nonwoven materials, liquid impermeable foams and liquid impermeable laminates are also contemplated for the articles as disclosed herein. The backing layer 3 may be breathable, implying that air and vapor may pass through the backing layer 3. It may be preferred that the backing layer is made from renewable raw materials.

Figure 2:
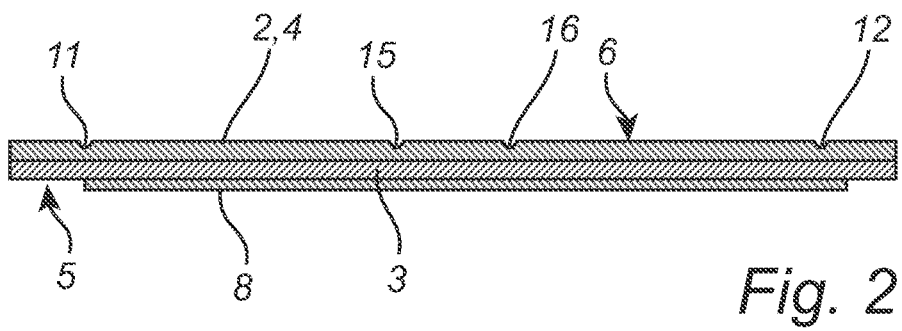
FIG. 2 shows a cross-section taken along the line II-II through the panty liner in FIG. 1.

As is shown in FIG. 2, the absorbent hygienic article 1 has a fastening member 8 on the garment-facing surface 5 of the absorbent hygienic article 1. The fastening member 8 is provided for allowing the absorbent hygienic article 1 to be fastened in the crotch portion of a pair of underpants or a hygienic pant and may e.g. be an adhesive fastening member, a friction fastener member or a hook-type fastener member as known in the art. The fastening member 8 may be protected by a release liner (not shown) during packaging and transport. The release liner is removed to expose the fastening member 8 before the absorbent hygienic article 1 is applied in the crotch portion of a pair of underpants. The fastening member 8 may alternatively be protected by a wrapper, also commonly referred to as a "single pack", which is releasable attached to the fastening member 8 and which is removed at the same time as the absorbent hygienic article 1 is taken out of the wrapper.

The fastening member 8 may be applied over the full outer surface of the the backing layer 3 or may be applied only in one or more selected areas of the outer surface of the liquid barrier layer 3. The fastening member 8 is an optional feature of the absorbent hygienic article.

The absorbent hygienic article 1 as disclosed herein is preferably thin and inconspicuous, the top layer preferably having a basis weight of at most 100 gsm, such as from 30 gsm to 100 gsm.

The absorbent hygienic article 1 which is shown in FIGS. 1 and 2 is provided with an embossed pattern in the form of a first pair of line embossings 11, 12 arranged along the longitudinal side edges 13, 14 of the absorbent hygienic article 1. A second pair of longitudinally extending line embossings 15, 16 are arranged centrally between the first pair of line embossings 11, 12. Line embossings generally promote fluid distribution along the lines and counteract fluid distribution perpendicular to the embossings.

A generally V-shaped embossing 17 is arranged at the front end edge 19 of the absorbent hygienic article 1 and an embossed flower 18 is arranged at the rear end edge 20 of the absorbent hygienic article 1. The second pair of line embossings 15, 16 are arranged to promote liquid spreading in the longitudinal direction of the absorbent hygienic article 1. The first pair of line embossings 11, 12 are arranged to retard liquid spreading to the longitudinal side edges 13, 14 of the absorbent hygienic article 1. The embossings 17, 18 which are placed at the end edges 19, 20 of the article have a fluid retarding function but are also intended to enhance the visual appearance of the absorbent hygienic article 1.

The absorbent hygienic article 1 may alternatively or in addition to embossings comprise functional and/or appearance enhancing print. The embossings which are shown in the FIGS. are optional to the absorbent hygienic article as disclosed herein. It is also to be understood that the embossings are not limited either to the number, shape or positioning shown in FIG. 1. Furthermore, if using embossings, they may be functional, appearance enhancing or a combination of functional and appearance enhancing embossings.

EXAMPLES AND DESCRIPTION OF TEST METHODS

Absorbent articles or isolated layers of the cellulosic fibrous web as disclosed herein can be subjected to testing according to the methods described herein.

Sample Preparation

Before testing, single articles or single layer web samples should rest flat and exposed for 24 hours in a stable laboratory environment set to 23° C. and 50% relative humidity. All subsequent testing should then be made in this same environment.

Determining Basis Weight and Density of a Web Sample

The web sample is weighed to the third decimal. The area of the sample is then determined, and basis weight is obtained by dividing the sample weight by the sample area. Basis weight is reported in the unit $g/m^2$ (gsm).

Web thickness is measured under a pressure of 0.5 kPa. A suitable thickness gauge should have an accuracy of 0.01 mm. Pressure is exerted from a square foot measuring 50×50 mm. The foot is gently lowered onto the sample, and a thickness value is read after 5 seconds.

Bulk is obtained by dividing the sample volume by the sample weight and should be reported in the unit $cm^3/g$.

Density is obtained by dividing the sample weight by the sample volume and should be reported in the unit kg/m$^3$.

A mean value is reported from measurements of ten representative samples.

Determining Spreading Distance and Rewet

An artificial menstrual fluid (AMF) according to the French standard AFNOR Q34-018 is used when testing.

For the spreading and rewet determinations, the sample should rest flat on a laboratory bench. Folded absorbent articles are unfolded, and carefully stretched flat. If testing a fibrous web in isolation, the web should be cut or punched to a rectangle measuring 50×100 mm. The length direction of the sample should coincide with the machine direction (MD) of the web. A smooth, liquid impermeable polyethylene film should be placed underneath the fibrous web.

The center point of the sample is identified (the point where the longitudinal centerline crosses the transverse centerline). AMF is introduced via a tube (internal diameter about 3 mm) connected to an automatic dispenser. The orifice of the tube is positioned perpendicular to the center point, with about 5 mm distance to the sample surface.

The sample is subjected to three 0.5 ml doses of AMF (i.e. 1.5 ml in total), introduced at a rate of 15 ml/min. When a dose has been absorbed (i.e. when there is no more free fluid on the sample surface), a stopwatch is started, and the next dose is introduced after 15 minutes.

Spreading length is measured 5 seconds after each dose has been absorbed. A ruler is placed along the longitudinal and transverse centerlines of the sample, and the extension of the wet area in the fibrous web (or article top layer) is determined. AMF that possibly spreads longer in the lateral side regions along the respective centerlines (such as in grooves or densified bonding patterns) is disregarded.

Rewet is measured 15 minutes after the third (last) dose has been absorbed. A stack of five pre-weighed filter papers (90×120 mm, 440 g/m$^2$ per sheet, Quality 167 from Munktell Ahlstrom or equivalent filter papers) is centered on top of the sample. A 5.5 kg weight with bottom dimension 90×120 mm (exerting a pressure of 5 kPa) is gently lowered on top of the stack. After 15 seconds the weight is removed, the filter papers are weighed, and AMF rewet is determined.

Mean values are reported from measurements of ten representative samples.

Tested Samples

S-1 (Reference sample): 70 gsm spunlace formed from a fibre blend of 35% viscose fibres, 56% polyester fibres (PET) and 9% polylactide acid fibres (PLA).

S-2: A foam-formed hydroentangled cellulosic fibrous web material having a basis weight of 50 gsm.

S-3: a two-layer foam-formed hydroentangled cellulosic fibrous web comprising a first lamina of 20 gsm foam-formed cellulosic fibrous web material and a second lamina of 50 gsm-foam formed cellulosic fibrous web material which were individually hydroentangled before being combined into a single web.

S-4: a two-layer foam-formed cellulosic fibrous web comprising a first lamina of 20 gsm foam-formed cellulosic fibrous web material and a second lamina of 50 gsm foam-formed cellulosic fibrous web material which were hydroentangled together, after having been combined into a single web.

The cellulosic fibrous webs used in samples S-2 to S-4 were all produced in the same manner with the foam-forming process disclosed in WO 2018/065668 A1. All samples had the same fibre composition of 15% viscose, commercial 1.7 dtex 10 mm Danufil, Kelheim, and 85% unrefined bleached softwood kraft pulp. All samples were hydroentangled on the same equipment under comparable conditions.

The results of the tests are set out in Table 1.

|  | Basis weight [g/m$^2$ (gsm)] | Bulk [cm$^3$/g] | Rewet [g] | Spreading CD/width [mm] after 1$^{st}$, 2$^{nd}$ and 3$^{rd}$ liquid insult | | | Spreading MD/length [mm] after 1$^{st}$, 2$^{nd}$ and 3$^{rd}$ liquid insult | | |
|---|---|---|---|---|---|---|---|---|---|
| S-1 Ref. | 69 | 12.3 | 1.1 | 28 | 38 | 47 | 42 | 52 | 63 |
| S-2 | 52 | 10.1 | 0.7 | 45 | 50* | 50* | 60 | 78 | 95 |
| S-3 | 72 | 10.1 | 0.6 | 36 | 48 | 50* | 48 | 70 | 85 |
| S-4 | 74 | 8.4 | 0.4 | 38 | 50* | 50* | 50 | 71 | 90 |

*a liquid spreading value of 50 mm in the CD/width direction is an indication that liquid has spread in the width direction of the sample all the way to the longitudinal side edges of the sample.

As can be seen in Table 1, all the samples S-2 to S-4 which are cellulosic fibrous web materials according to the invention as disclosed herein have excellent rewet and liquid spreading properties. It is noted that the conventional polyester/viscose material which was used as the reference had considerably higher rewet than all the samples according to the invention, including the S-2 sample having a lower basis weight than the other samples.

The invention claimed is:

1. An absorbent hygienic article for absorbing body fluids, the article comprising a liquid absorbent top layer and a backing layer, the top layer and the backing layer being made from roll materials and being joined together, wherein the top layer consists of a cellulosic fibrous web, the fibres in the cellulosic fibrous web consisting of a mixture of cellulose fibres, the mixture comprising cellulose pulp fibers, and at least one of regenerated cellulose fibres and natural cellulose staple fibres, the cellulosic fibrous web being a foam-formed, hydroentangled cellulosic fibrous web.

2. An absorbent hygienic article according to claim 1, wherein the regenerated cellulose fibres and/or the natural cellulose staple fibres are staple fibres having a length within the range of from 2 to 20 millimeter and a linear density in the range of from 0.3 to 3 dtex.

3. An absorbent hygienic article according to claim 1, wherein the mixture of cellulose fibres includes viscose fibres.

4. An absorbent hygienic article according to claim 1, wherein the mixture of cellulose fibres is constituted by 2 to 50% by weight of regenerated cellulose fibres or natural cellulose staple fibres based on a total weight of the mixture of cellulose fibres.

5. An absorbent hygienic article according to claim 1, wherein the top layer has a basis weight of from 30 gsm to 100 gsm.

6. An absorbent hygienic article according to claim 1, wherein the cellulosic fibrous web has a bulk in the range of 7.5 to 11 cm³/g.

7. An absorbent hygienic article according to claim 1, wherein the absorbent hygienic article has a rewet of less than 1 gram as measured according to the method disclosed herein.

8. An absorbent hygienic article according to claim 1, wherein the cellulosic fibrous web has a liquid spreading capacity in a machine direction of the cellulosic fibrous web of 75 millimeters or more as measured after three insults of test liquid in accordance with the test method disclosed herein.

9. An absorbent hygienic article according to claim 1, wherein the absorbent hygienic article has a liquid spreading capacity in a cross machine direction of the cellulosic fibrous web of 30 millimeters or more as measured after a first insult of test liquid and of 45 millimeters or more as measured after two insults of test liquid, the measurements being made in accordance with the test method disclosed herein.

10. An absorbent hygienic article according to claim 1, wherein the backing layer is constituted by renewable raw materials.

11. An absorbent hygienic article according to claim 1, wherein a sample of the cellulosic fibrous web having a length in the machine direction of 100 millimeters and a width in the cross machine direction of 50 millimeters and a basis weight of 50 gsm to 70 gsm has a wet area of 3500 mm² or more as measured according to the test method as disclosed herein.

12. An absorbent hygienic article according to claim 1, wherein the top layer and the backing layer are the only constituent layers of the absorbent hygienic article.

13. An absorbent hygienic article according to claim 1, wherein the absorbent hygienic article is a panty liner.

14. An absorbent hygienic article according to claim 1, wherein the absorbent hygienic article is an underwear protector, an underarm protector, a bib, a seat cover, a place mat, under pants, or a bed protector.

15. An absorbent hygienic article according to claim 1, wherein a user-facing surface of the absorbent hygienic article is provided with an embossed pattern, a dimpling pattern, a printed pattern or a combination of one or more of an embossed pattern, a dimpling pattern, and a printed pattern.

16. An absorbent hygienic article according to claim 1, wherein a sample of the cellulosic fibrous web having a length in the machine direction of 100 millimeters and a width in the cross machine direction of 50 millimeters and a basis weight of 50 gsm to 70 gsm has a wet area of 4000 mm² or more as measured according to the test method as disclosed herein.

* * * * *